United States Patent [19]
Oh et al.

[11] Patent Number: 5,494,827
[45] Date of Patent: Feb. 27, 1996

[54] METHOD USING AZIDE CATALYST FOR PEROXYOXALATE CHEMILUMINESCENCE REACTION

[75] Inventors: Sang Kon Oh; Seung Hee Cha, both of Daejon, Rep. of Korea

[73] Assignee: Agency for Defense Development, Daejon, Rep. of Korea

[21] Appl. No.: 259,237

[22] Filed: Jun. 13, 1994

Related U.S. Application Data

[63] Continuation of Ser. No. 143,347, Oct. 26, 1993, abandoned.

[30] Foreign Application Priority Data

Mar. 31, 1993 [KR] Rep. of Korea .................... 5431/1993

[51] Int. Cl.$^6$ .................................................. G01N 21/76
[52] U.S. Cl. .......................................... 436/172; 436/135
[58] Field of Search ...................................... 436/135, 172, 436/63, 8, 129, 131, 166; 435/28

[56] References Cited

U.S. PATENT DOCUMENTS 4,647,532  3/1987  Watanabe et al. ...................... 435/28
5,225,584  7/1993  Brooks et al. .......................... 558/189

OTHER PUBLICATIONS

Imai, K. "Chemiluminescence Detection System for High-Performance Liquid Chromatography" Methods in Enzymology, vol. 133 (1986) pp. 435–449.

Seitz, W. R. "Chemiluminescence Detection of Enzymically Generated Peroxide" Methods in Enzymology, vol. 57 (1978) pp. 445–462.

Sang Kon Oh and Seung Hee Cha, *Analytical Biochemistry* 218:222–4, 1994.

Primary Examiner—Jeffrey R. Snay
Attorney, Agent, or Firm—Darby & Darby

[57] ABSTRACT

An azide catalyst for peroxyoxalate chemiluminescence reactions is provided, which catalyzes a reaction of an oxalic acid ester compound with a peroxide in a solvent to produce 1,4 dioxetane dione as an intermediate that is subsequently decomposed catalytically by a fluorescent agent to emit light. The catalyst improves not only luminous efficiency such as luminous time and luminous intensity but also reaction of the intermediate with a peroxide.

7 Claims, 3 Drawing Sheets

METHOD USING AZIDE CATALYST FOR PEROXYOXALATE CHEMILUMINESCENCE REACTION

This is a continuation of application Ser. No. 08/143,347, filed Oct. 26, 1993, now abandoned.

BACKGROUND OF THE INVENTION

1. Field of the Invention

The present invention relates in general to a peroxyoxalate chemiluminescence reaction, and more particularly to improvements in luminous time and luminous intensity by adopting an azide compound as a catalyst for the reaction and to various applications utilizing the same.

2. Description of the Prior Art

An analysis method utilizing a chemiluminescene reaction makes it possible to analyze quantitatively all materials which are in relation with a chemiluminescence reaction in a intermediate stage or a last stage of the reaction. It has higher sensitivity than any other than current chemical analysis method and is used in a variety of fields. For example, it is applied for a laboratory analysis test and to a detector of an analyzing equipment. Accordingly, its applicability has attracted attention greatly.

In a chemiluminescence reaction, the reaction associated with luminol, lucigenin, peroxyoxalate and the like has been known in the art. Among these, luminol and peroxyoxalate are representative of the compounds, that are applicable to a practical analysis method.

It has been recognized in the art that a peroxyoxalate chemiluminescence reaction is most effective in the chemiluminescence reactions. As a general reaction path of the peroxyoxalate chemiluminescence reaction, there is an example as follows:

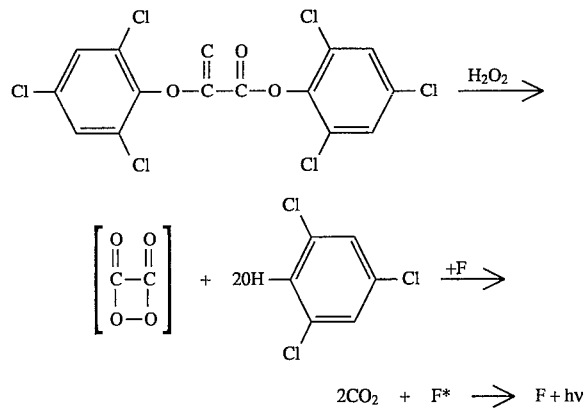

wherein F is a fluorescent agent; and
$F^x$ is a excited state of F.

In the meantime, considering the peroxyoxalate chemiluminescence reaction, under the existence of a fluorescent agent, an oxalic acid ester compound and a related compound dissolved in a solvent reacts with a peroxide to form 1,4-dioxetane dione, an intermediate, which is then, decomposed by the fluorescent agent to emit light. This chemiluminescence according to the chemiluminescence reaction path shows a relative high efficiency in an alkaline liquid as well as in a neutral liquid and even in a weak acid liquid. As a result, it is widely applied to an analysis test for biological sample such as hydrogen peroxide, peroxygenase, amino acid and the like, as well. In addition, this chemiluminescence reaction method has higher sensitivity than any other quantitative analysis method and has such an advantage that it utilizes various reagents. A variety of analyzing equipments making use of it have been developed. Furthermore, the chemiluminescence reaction is also applied for the principle of a light source and several light sources utilizing it have been already developed and used.

Unlike the chemiluminescence reaction using luminol, however, the chemiluminescence reaction associated with oxalic acid ester compounds and related compounds requires an organic solvent such as an acetonitrile solvent, an ether solvent, an alcohol solvent and the like in order to dissolve the compounds. However, these solvents contain many problems therein such that the compounds have very insignificant solubilities for the solvents and are not stable in the solvents because they decompose spontaneously.

In addition, even oxalic acid ester compound dissolved in a proper solvent, when it is mixed with an aqueous solution in which most analytes are contained, is precipitated because its solubility becomes lowered and thence, it is difficult to induce a complete reaction. Therefore, when the chemiluminescence reaction using oxalic acid ester compounds and related compounds is utilized for a variety of chromatophotometries and other analysis methods, an additional apparatus such as a mixer and the like is needed to prevent such incomplete dissolution and to perform the mixing in harmony. Especially, when the water content of an analyte is high, such solubility decrease prohibits the chemiluminescence analysis method from being applied to the analyte in spite of its high analysis sensisitivity. Furthermore, encountering the analyte with a high water-content, there is always involved a problem in that a luminuous efficiency becomes lowered greatly. The aforementioned problems are serious obstacles to the development of light source for a variety of purposes.

In order to surmount the problems, novel compounds which are capable of being dissolved in water has received careful and much study and investigation. However, the resultant compounds, yet developed has also such problems that most of it is unstable and the luminous flux or intensity thereof is low.

In the meanwhile, several catalysts have been used to increase the luminous intensity and luminous efficiency. They are mostly basic catalysts of which triethylamine and imidazole are representative. However, these basic catalysts can play a role in increasing only reaction rate by changing the hydrogen ion concentration of solution and thus, the aforementioned problems can not be solved thereby. Besides the basic catalysts, metal ions and metal-containing proteins are known as reactive catalysts, but the catalytic effects thereof are unsatisfied and even negligible.

SUMMARY OF THE INVENTION

For solving the above-mentioned problems, the present inventors have recognized that there exists a need for a catalyst capable of stabilizing oxalic acid compounds and related compounds in an organic solvent and increasing the solubility of the compounds when they are mixed into an aqueous solution, and have researched into the catalyst and then found that azide salts and derivatives thereof are endowed with such functions as the catalyst for peroxyoxalate chemiluminescence reaction must possess.

Accordingly, it is an object to provide an azide catalyst for peroxyoxalate chemiluminescence reaction in which under the existence of a fluorescent agent, an oxalic acid ester compound and/or a related compound dissolved in a solvent reacts with a peroxide to form 1,4-dioxetane dione, an intermediate, which is then, decomposed by the fluorescent agent to emit light.

According to an embodiment of the present invention, there may be provided an effective analyzing equipment remarkably improved in analysis sensitivity, which makes use of the peroxyoxalate chemiluminescence reaction using the present azide compound and derivatives thereof so as to increase the luminous intensity and the luminous amount thereof.

According to another embodiment of the present invention, there may be provided a light source for various purposes, which makes use of the peroxyoxalate luminescence reaction using the present azide catalyst and derivatives thereof, so as to have a much longer luminous time than a conventional light source.

According to a further embodiment of the present invention, there may be provided an analysis method and reaction, which comprise making use of the peroxyoxalate chemiluminescence reaction using the present azide catalysts and derivatives thereof.

These and other objects and advantages of the present invention will become more apparent as the following description proceeds.

To the accomplishment of the foregoing and related ends, the invention, then, comprises the features hereinafter fully described in the specification and particularly pointed out in the claims, the following description and the annexed drawing setting forth in detail a certain illustrative embodiment of the invention, this being indicative, however, of but one of the various ways in which the principles of the invention may be employed.

DETAILED DESCRIPTION OF THE INVENTION

Figure 1:
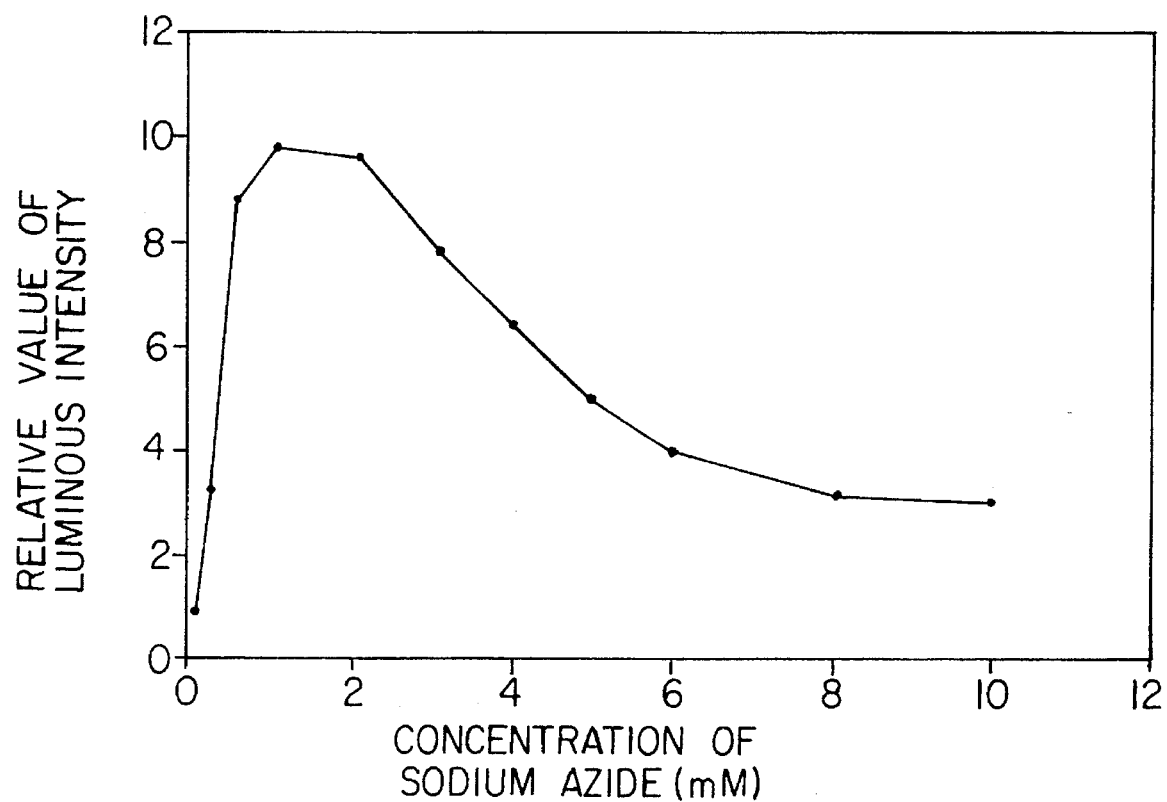
FIG. 1 is a graph illustrating luminous intensity with respect to the concentration of a sodium azide catalyst according to the present invention in a reaction solution consisting of Tris-HCl buffer and acetonitrile with equal volume.

In a peroxyoxalate chemiluminescence reaction, the present invention adopts an azide compound instead of a conventional basic compound as a catalyst for the reaction so as to perform a substitution reaction of the present catalyst for an oxalic acid ester compound, a starting material, through which there is obtained an oxalic acid ester compound substituted with one or two azide group(s), an intermediate. The substituted compound becomes more soluble in water due to the azide group's hydrophilicity and thence comes to have greater solubility in various solutions. As a result, not only luminous efficiency such as luminous time and luminous intensity is improved remarkably but also a satisfactory reaction of the intermediate on a peroxide is performed even when encountering an analyte having high water-content. In addition, even though water content of a solution for the chemiluminescence reaction exceeds 95%, the reactants are prevented from being precipitated. Furthermore, an additional mixer is unnecessary.

Suitable examples of the azide compounds according to the present invention include metal azide such as sodium azide ($NaN_3$), potassium azide ($KN_3$) and calcium azide ($Ca(N_3)_2$); substituted or unsubstituted aliphatic azide compound such as chloroethyl azide or butyl azide; substituted or unsubstituted aromatic azide compound such as azidonitrobenzene, 2-azidoaniline or phenyl azide; cycloaliphatic azide compound such as azidocycloethane; aromatic acylazide compound such as phenacyl azide; other organic derivative thereof such as vinyl azide and aryl azide; and inorganic derivative thereof such as cyanogen azide, β-iodoazide. Preferred catalysts are the metallic salts of azide and more preferred catalyst is the sodium azide. However, any compound that is capable of forming a nucleophilic azide group naturally or artificially may be used in the present invention. Thus, hydrogen azide and azide ion ($N_3^-$) may be used as the catalyst according to the present invention.

Suitable examples of the oxalic acid ester compound used in the chemiluminescence reaction include compounds which are used generally, such as anhydrous oxalic acid amides and o-acyl-hydroxylamines. Preferred oxalic acid ester compound is bis-2,4,6-trichlorophenyl oxalate (hereinafter "TCPO").

There serve liquid and solid peroxides including hydrogen peroxide as examples of the peroxides which may be used in the peroxyoxalate chemiluminescence reaction in accordance with the present invention. Hydrogen peroxide is preferable.

Suitable examples of the fluorescent agents used in the chemiluminescence reaction according to the present invention include perylene, 9,10-diphenylanthracene, pyrene, DNS-amino acids, polycyclic aromatic hydrocarbons, amine compounds, and various aromatic hydrocarbons. Preferred fluorescent agent is pyrene.

In an embodiment according to the present invention, sodium azide as a catalyst and TCPO as an oxalic acid compound are dissolved with equal mole concentration in various solvents, for example, acetonitrile, water and alcohol, and react therebetween at room temperature for 1 minute to produce a product, which is then subjected to the treatment of separation with a liquid chromatography so as to analyze and ascertain the product. The separated product is further treated to an infrared spectrometry, an ultraviolet spectrometry, a hydrogen nuclear magnetic resonance analysis, and a mass spectrometry. From the above tests, a mechanism for the chemiluminescence reaction is established as follows:

Step 1

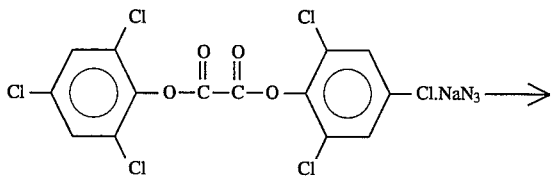

-continued

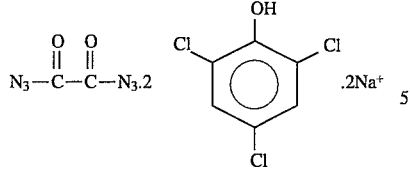

or

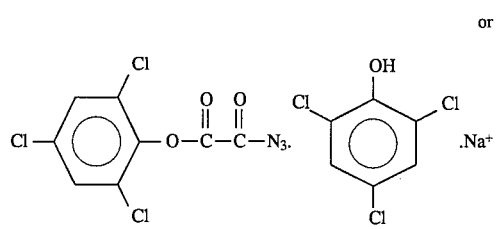

Step 2

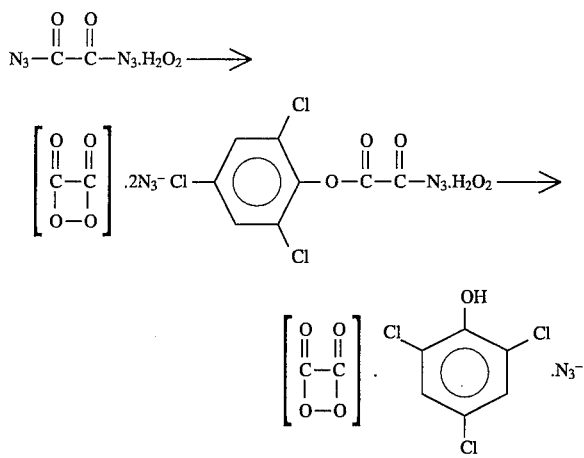

Step 3

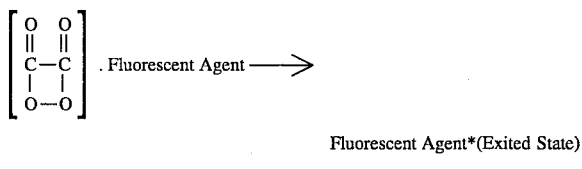

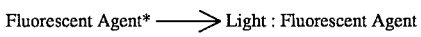

Fluorescent Agent* ⟶ Light : Fluorescent Agent

In the meanwhile, considering the great increase of luminous amount in accordance with the present invention, it is presumed that an intermediate having an energy higher than the 1,4-dioxetane dione may be generated in step 2 of the above mechanism.

The following examples are include merely to aid in the understanding of the present invention, and variations may be made by one skilled in the art without departing from the spirit and scope of the present invention.

EXAMPLE 1

Analysis for Luminous Intensity according to NaN$_3$ Amount 6 mg/ml of TCPO and 0.1 mg/ml of pyrene were dissolved in an acetonitrile solvent. Separately, sodium axides were dissolved in a buffer solution including 10 μM of hydrogen peroxide in the concentration range of 0.1 to 10 mM and then, 5 ml of each of the solutions was placed in a glass bottle. Into this bottle, the acetonitrile solution were mixed with equal volume. Instantly, the mixed solution was placed in a photometer equipped with a recorder to measure the luminous amount and intensity.

The result is illustrated as shown in FIG. 1.

EXAMPLE 2

A variety of azide compounds were added into an acetonitrile solution including 6 mg/ml of TCPO and 0.1 mg/ml of pyrene. A buffer solution containing 10 μM of hydrogen peroxide was mixed into the acetonitrile solution with equal volume. The mixed solution was tested in a manner similar to that in Example 1. Their results are given as shown in Table 1.

TABLE 1

| Compound | Relative Luminous Intensity |
| --- | --- |
| NaN$_3$ | 100 |
| KN$_3$ | 94.0 |
| Ca(N$_3$)$_2$ | 96.0 |
| Butyl azide | 14.4 |
| Chloroethyl azide | 12.4 |
| Phenyl azide | 32.4 |
| Azidocyclophentane | 12.1 |
| Phenacyl azide | 10.8 |
| Cyanogen azide | 64.2 |
| Azidonitrobezene | 16.0 |
| 2-azidoaniline | 11.0 |
| B-iodoazide | 22.4 |

EXAMPLE 3

Analysis for the Reactivity of Oxalic Acid on Azide

An acetonitrile solution containing 6 mg/ml of TCPO was mixed into a buffer solution containing 3 mg/ml of azide with equal volume and reacted therebetween for 5 minutes at room temperature to produce a product. The product was then subjected to the treatment of thin layer chromatograph so as to be separated. The separated product was further treated to an infrared spectrometry, an ultraviolet spectrometry, hydrogen nuclear magnetic resonance analysis, and mass spectrometry. As a result, it was ascertained that 2,4,6-trichlorophenol was produced.

In addition, a compound substituted with one or two N$_3$ group(s) in the above mechanism was certified by an infrared spectrometry and a high speed liquid chromatograph. The substituted compound resulted from a short reaction time within 10 seconds.

EXAMPLE 4

Comparative Analysis for Catalytic Powers of Azide Compound and Conventional Catalyst At the concentration of a best catalytic efficiency, sodium azide (1.0 mM) according to the present invention and comparative triethylamine (0.2 mM), a conventional catalyst, were tested in a manner similar to that in Example 1.

Figure 2:
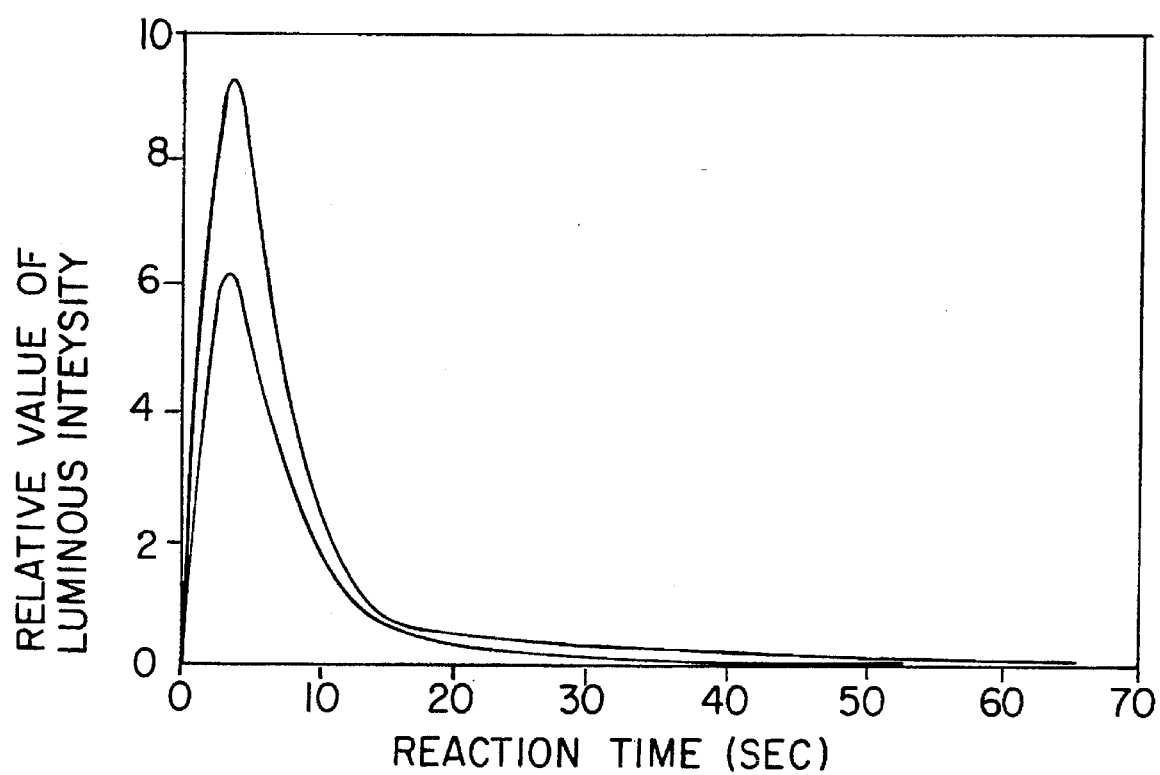
FIG. 2 is a graph illustrating luminous intensity of the present sodium azide catalyst, a conventional triethylamine catalyst and none with respect to reaction times in a reaction solution consisting of Tris-HCl buffer and acetonitrile with equal volume.

The result is illustrated as shown in FIG. 2.

EXAMPLE 5

Affect of Azide Compound on Quantitative Analysis for Hydrogen Peroxide

The amount of hydrogen peroxide to be added into a buffer solution was determined in the range of $10^{-1}$ to $10^{-9}$M and then tested in a manner similar to that in Example 1. With regard to comparison group, sodium azide was not added into it.

The result is given as shown in the following Table 2.

EXAMPLE 6

Affect of Azide Compound on Quantitative Analysis for Oxidizing Enzyme

Glucose oxidase and choline oxidase were added into 0.001M and 0.1M of phosphate buffer solution, respectively. 0.5 mM of glucose and 0.5 mM of acetylcholine was added into the two solutions, respectively, and reacted therebetween at 35° C. for 10 minutes. Thereafter, luminous amounts depending on the amount of hydrogen peroxide generated in the respective solution were measured in a manner similar to that in Example 5.

The results are given as shown in Table 2.

TABLE 2

Comparison of the Affects of Azide Compound on the Analysis for Hydrogen peroxide and Oxidizing Enzyme.

| Analyte | Analysis Sensitivity | |
|---|---|---|
| | Azide | None |
| Hydrogen peroxide | $10^{-9}$ M | $10^{-7}$ M |
| Glucose Oxidase | $2.6 \times 10^{-4}$ unit | $5 \times 10^{-3}$ unit |
| Choline Oxidase | $1.2 \times 10^{-3}$ unit | $1 \times 10^{-2}$ unit |

EXAMPLE 7

Analysis for the Luminous Efficiency and Luminous Time According to the Amount of Azide Compound $2.5 \times 10^{-4}$M of sodium azide was dissolved in dimethylphthlate together with $1.25 \times 10^{-2}$M of hydrogen peroxide. Separately, 6 mg/ml of TCPO and 0.1 mg/ml of 9,10-diphenyl anthracene were dissolved in dimethylphthalate. The two solutions were mixed with equal volume of 200 μl and then luminous amount was measure in a manner similar to that in Example 1.

Figure 3:
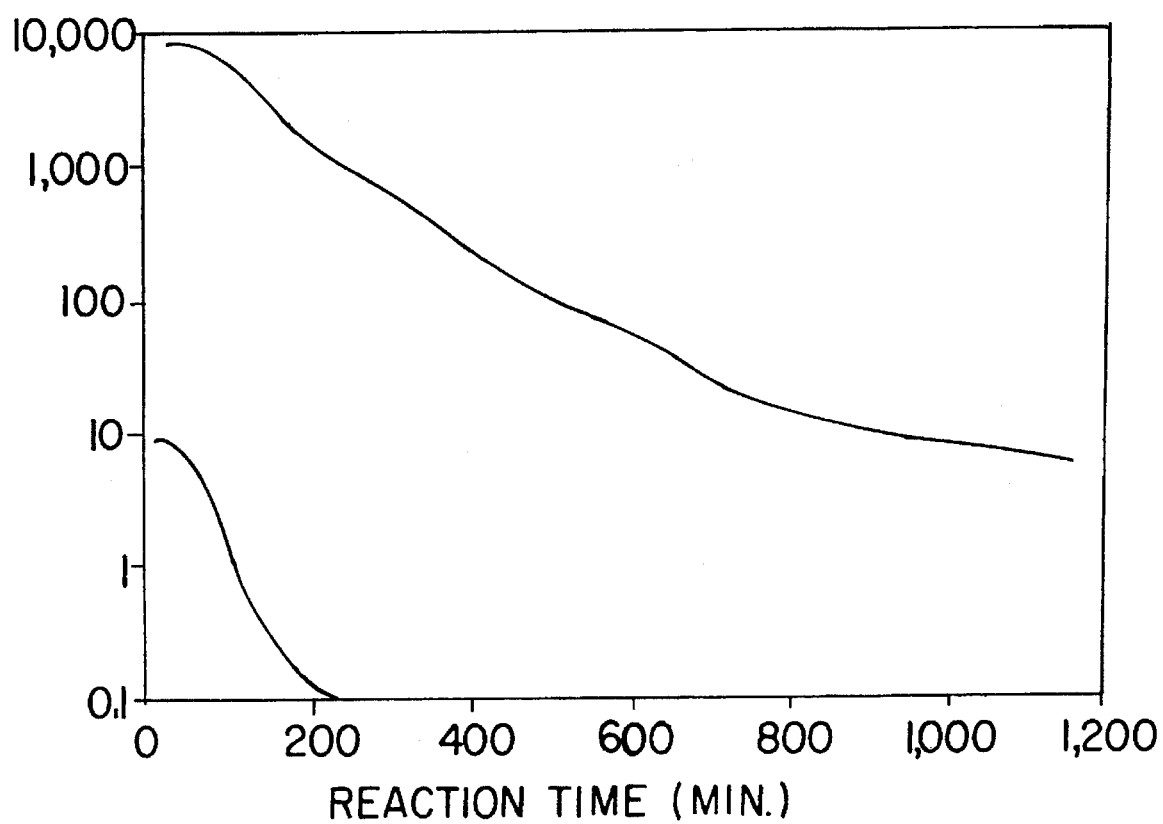
FIG. 3 is a graph illustrating luminous intensity of sodium azide according to the present invention with regard to reaction times in a dimethylphthalate solution.

The result is given as illustrated in FIG. 3.

As indicated in the annexed drawings, an azide compound, that is, a catalyst according to the present invention, when it is applied to chemiluminescence reaction, is capable of increasing remarkably a luminous intensity and a luminous efficiency as well as a luminous time. In addition, this increase permits various light sources to be developed.

Furthermore, the use of the azide compounds suggested in the present invention improves the solubility of an ester compound, which is one of the most troublesome problems in conventional chemiluminescence analysis methods. Namely, according to the present invention, there is solved the problems that, in a conventional peroxalate chemiluminescence reaction system, oxalic acid ester compound dissolved in even an appropriate solvent, when it is mixed with an aqueous solution in which most analytes are contained, is precipitated because its solubility becomes lowered and thence, it is difficult to induce a complete reaction. As a result, the enhanced solubility provides such a concomitant effect that when the chemiluminescence reaction using oxalic acid ester compounds and related compounds is utilized for a variety of chromatophotmetries and other analysis methods, an additional apparatus such as a mixer and the like is not needed any more to prevent such incomplete dissolution and to perform the mixing in harmony.

Therefore, as described hereinbefore, in accordance with the present invention, analysis sensitivity for various analytes is improved significantly, and a precipitation phenomenon does not occur even in the reaction solution which has water content of above 95%, so that reaction rate may be controlled easily. Therefore, the chemiluminescence reaction according to the present invention is believed to have great influence on the development for related analyzing equipments.

What is claimed is:

1. A method for conducting a peroxyoxalate chemiluminescence reaction, which consists essentially of catalyzing with an azide catalyst the reaction, in a solvent, of oxalic acid ester and a peroxide in the presence of a fluorescent agent to produce an intermediate, and decomposing said intermediate with the fluorescent agent to emit light.

2. A method as claimed in claim 1, wherein said oxalic ester compound is bis-2,4,6-trichlorophenyl oxalate.

3. A method as claimed in claim 1, wherein the peroxide is hydrogen peroxide.

4. A method as claimed in claim 1, wherein the fluorescent agent is pyrene.

5. A method as claimed in claim 1, wherein the solvent is selected from the group consisting of acetonitrile, water, alcohols, and mixtures thereof.

6. A method as claimed in claim 1, wherein the azide, catalyst is selected from the group consisting of $NaN_3$, $KN_3$, $Ca(N_3)_2$, butyl azide, chloroethyl azide, phenyl azide, azidocyclopentane, phenacyl azide, cyanogen azide, azidonitrobenzene, 2-azidoaniline, and β-iodoazide.

7. A method as claimed in claim 1, wherein the intermediate is 1,4-dioxetane dione.

* * * * *